(12) United States Patent
Baroud et al.

(10) Patent No.: US 9,816,133 B2
(45) Date of Patent: Nov. 14, 2017

(54) MICROFLUIDIC PROCESS FOR TREATING AND ANALYSING A SOLUTION CONTAINING A BIOLOGICAL MATERIAL AND CORRESPONDING MICROFLUIDIC CIRCUIT

(71) Applicants: Ecole Polytechnique, Palaiseau (FR); CENTRE NATIONAL DE LA RECHERCHE SCIENTIFIQUE, Paris (FR)

(72) Inventors: Charles Baroud, Paris (FR); Remi Dangla, Paris (FR); Paul Abbyad, Santa Clara, CA (US); Silvan Turkcan, Paris (FR)

(73) Assignees: École Polytechnique, Palaiseau (FR); Centre national de la recherche scientifique, Paris (FR)

( * ) Notice: Subject to any disclaimer, the term of this patent is extended or adjusted under 35 U.S.C. 154(b) by 0 days.

(21) Appl. No.: 14/434,390

(22) PCT Filed: Oct. 8, 2013

(86) PCT No.: PCT/EP2013/070966
§ 371 (c)(1),
(2) Date: Apr. 8, 2015

(87) PCT Pub. No.: WO2014/056930
PCT Pub. Date: Apr. 17, 2014

(65) Prior Publication Data
US 2015/0267246 A1 Sep. 24, 2015

(30) Foreign Application Priority Data

Oct. 8, 2012 (FR) ..................................... 12 59566

(51) Int. Cl.
*B01L 3/00* (2006.01)
*C12M 1/00* (2006.01)
(Continued)

(52) U.S. Cl.
CPC .......... *C12Q 1/686* (2013.01); *B01L 3/50273* (2013.01); *B01L 3/502761* (2013.01);
(Continued)

(58) Field of Classification Search
CPC ........ B01L 3/502; B01L 7/52; B01L 2200/06; B01L 2300/08; C12Q 1/68; C12M 1/00; C40B 60/08
(Continued)

(56) References Cited

U.S. PATENT DOCUMENTS 7,943,671 B2  5/2011  Herminghaus et al.
8,136,553 B2  3/2012  Baroud et al.
(Continued)

FOREIGN PATENT DOCUMENTS

DE   102005037401      2/2007
DE   10 2005 037 401 A  12/2008
(Continued)

OTHER PUBLICATIONS

Hatch et al. "1 million droplet array with wide field fluorescence imaging for digital PCR", 2011, Lab Chip, vol. 11, pp. 3838-3845.
(Continued)

*Primary Examiner* — Narayan Bhat
(74) *Attorney, Agent, or Firm* — Morgan, Lewis & Bockius LLP

(57) ABSTRACT

Provided herein are microfluidic circuits that include at least one device for forming a quantity of drops of a solution in a carrier fluid and at least one storage zone for storing drops produced by the microfluidic device. Such microfluidic
(Continued)

circuits are useful, for example, for the analysis of a solution containing a biological sample.

8 Claims, 6 Drawing Sheets

(51) Int. Cl.
*E03B 1/00* (2006.01)
*F17D 1/00* (2006.01)
*C12Q 1/68* (2006.01)
*B01L 7/00* (2006.01)

(52) U.S. Cl.
CPC ... *B01L 3/502784* (2013.01); *B01L 3/502792* (2013.01); *B01L 7/52* (2013.01); *B01L 2200/0642* (2013.01); *B01L 2200/0652* (2013.01); *B01L 2200/0668* (2013.01); *B01L 2300/0816* (2013.01); *B01L 2300/0864* (2013.01); *B01L 2300/0867* (2013.01); *B01L 2400/0457* (2013.01); *B01L 2400/0463* (2013.01); *B01L 2400/084* (2013.01)

(58) Field of Classification Search
USPC ............ 422/502, 504; 435/6.1, 283.1; 137/2
See application file for complete search history.

(56) References Cited

U.S. PATENT DOCUMENTS

| 8,206,994 | B2 | 6/2012 | Baroud et al. |
| 9,133,009 | B2 | 9/2015 | Baroud |
| 2005/0063875 | A1* | 3/2005 | Schatz .................. G21K 1/006 422/400 |
| 2008/0314761 | A1 | 12/2008 | Herminghaus et al. |
| 2010/0190263 | A1 | 7/2010 | Srinivasan et al. |
| 2011/0190146 | A1* | 8/2011 | Boehm ............. B01L 3/502784 506/7 |
| 2012/0315203 | A1 | 12/2012 | Baroud |
| 2013/0078164 | A1 | 3/2013 | Baroud et al. |

FOREIGN PATENT DOCUMENTS

| FR | 2873171 | 1/2006 |
| FR | 2901717 | 12/2007 |
| WO | 2010036352 | 4/2010 |
| WO | 2011039475 | 4/2011 |
| WO | WO 2011/121220 A | 6/2011 |
| WO | 2011121220 | 10/2011 |

OTHER PUBLICATIONS

Beer et al., "On-chip, real-time, single-copy polymerase chain reaction in picoliter droplets", 2007, Analytical chemistry, American chemical society, vol. 79, N. 22, pp. 8471-8475.
Ralf Seemann et al., "Droplet based microfluidics", 2011, Reports on progress in physics, Institute of physics publishing, vol. 75, N. 1, p. 16601.
N. Reginald Beer et al., On-Chip, Real-Time, Single-Copy Polymerase Chain Reaction in Picoliter Droplets, Book, Nov. 15, 2007, pp. 8471-8475, vol. 79 No. 22.
Ralf Seemann et al., Droplet Based Microfluidics, Article, Dec. 22, 2011, pp. 1-42, IOP Publishing Ltd., United Kingdom and United States.

* cited by examiner

B-B

C-C

MICROFLUIDIC PROCESS FOR TREATING AND ANALYSING A SOLUTION CONTAINING A BIOLOGICAL MATERIAL AND CORRESPONDING MICROFLUIDIC CIRCUIT

CROSS-REFERENCE TO RELATED APPLICATIONS

This application is a US National Phase of International Patent Application No. PCT/EP2013/070966, filed Oct. 8, 2013, which claims priority to French Patent Application No. 1259566, filed on Oct. 8, 2012, the disclosure of which is incorporated herein in its entirety for all purposes.

STATEMENT REGARDING FEDERALLY SPONSORED RESEARCH OR DEVELOPMENT

Not applicable.

BACKGROUND OF THE INVENTION

The present invention relates to a process for treating and analysing a solution containing a biological material, using a microfluidic method wherein the solution is divided into a plurality of drops.

The invention also relates to a microfluidic circuit, suitable for handling very small quantities of fluids, particularly suitable for using such a process.

FR-2873171, FR-2901717, WO-2011/121220 and WO-2011/039475, held by the applicants, describe microfluidic processes suitable for producing and handling, in suitable microfluidic circuits, drops of a first fluid placed in a second fluid, referred to as a carrier fluid. The first fluid is generally an aqueous solution, divided into drops having a volume in the range of 10 to 100 $\mu m^3$. The carrier fluid is generally oil, to which is optionally added a surfactant product suitable for preventing the spontaneous merging of the drops of fluid handled, if they come into contact.

The use of such microfluidic processes has been proposed for applying treatments to a solution containing a biological material, followed by analyses of the treated solution. It has particularly been envisaged to use such techniques for implementing polymerase chain reaction amplification techniques (frequently referred to using the acronym "PCR") suitable for copying large numbers of a nucleic acid sequence, such as DNA (acronym of "Deoxyribonucleic Acid") or RNA (acronym for "Ribonucleic Acid"). To carry out this amplification, a solution containing a small quantity of nucleic acid is prepared, subjected to a heat treatment referred to as thermocycling, consisting of cyclic temperature variations. These temperature variations enable forced duplications of the nucleic acid molecules present in the solution. It is thus possible to increase the nucleic acid concentration in the solution considerably.

These polymerase chain reaction amplification methods, which can be divided into a large number of variants, are well-known to those skilled in the art of molecular biology. Polymerase chain reaction amplification methods using microfluidic processes for dividing the solution containing nucleic acid into numerous low-volume portions, before amplification, are also known per se by those skilled in the art, and are commonly referred to as "digital PCR".

Such a digital PCR process is particularly known from the document WO 2010/036352. According to the process, a flow, or flux, of carrier fluid is used to divide the solution containing the nucleic acid into a large quantity of drops. The concentration of the nucleic acid in the solution is chosen so that, statistically, a small number of drops contain a molecule of the nucleic acid under test. The drops are placed in a vessel to undergo thermocycling, suitable for the polymerase chain reaction amplification of the nucleic acid. They are then introduced into a channel to be analysed optically, in succession, so as to detect those containing, prior to thermocycling, at least one occurrence of the nucleic acid, and containing after this thermocycling a large quantity of this nucleic acid.

This process requires the use of numerous items of costly equipment for, on one hand, producing the drops, and for performing the thermocycling, and finally for analysing the drops after the thermocycling thereof. Moreover, these successive operations are long and require extensive expertise. Polymerase chain reaction amplification according to this process is consequently long, costly, and can only be performed by specially trained operatives.

Moreover, when a flow of carrier fluid is used for producing drops from the sample of solution containing the nucleic acid, the first drops, produced during a transitory phase, have unsuitable sizes. Only the drops produced during a second phase, which have more homogeneous sizes, can be used for the polymerase chain reaction amplification. This process thus involves the loss of a significant proportion of the initial sample of solution containing the nucleic acid. Further losses of a portion of this solution are induced by the transfers required between various vessels. This process may thus give rise to significant losses of the sample, that may be in the region of 25%. The biological samples being sometimes extremely rare and costly, such a loss represents a major drawback.

A further digital PCR process using drops is also known from the article "1-Million droplet array with wide field fluorescence imaging for digital PCR", by Hatch, Fisher, Tovar, Hsieh Lin, Pentoney, Yan and Lee (Lab Chip, 2011, 11, 3838), wherein the drops of solution containing the nucleic acid are created by eight successive divisions of one drop into two drops of equal size. These successive divisions are suitable for creating, from one initial drop, 256 drops of equal size which are propelled into an extra-wide flat channel. After the production of a large number of these drops, a significant portion of the channel may be filled. The channel and the drops contained therein may then be subjected to thermocycling suitable for the polymerase chain reaction. Thereafter, the analysis of the various drops may be carried out directly, without removing the drops from the channel, by means of optical observation of the drops through a transparent wall of the channel.

This process also has some drawbacks. In this way, it requires having an initial drop of a clearly defined size, suitable for being divided into drops of suitable size for subsequent processing and measurement. However, the method used for producing initial drops, by dividing a flow of solution under the action of a flow of carrier fluid, implies a transitory phase at the start of drop production, during which the flows of solution containing the nucleic acid and the carrier fluid need to balance out. The drops formed during this transitory phase thus have an unsuitable size. The successive divisions of these initial drops give rise to the introduction into the channel of a large number of drops of unsuitable size, which cannot be validly analysed. Consequently, only a portion of the sample of biological fluid can be analysed, another portion, representing approximately 10% of the sample, being lost.

Moreover, the drop only being suitable for being produced and divided under the action of a carrier fluid flow, a large quantity of this carrier fluid is introduced into the channel at the same time as the drops. Consequently, the concentration of drops in the carrier fluid, in this channel, is not optimal.

Finally, this process, requiring the balancing of a flow of solution containing the nucleic acid and a flow of biological fluid, is relatively complex to implement and requires special expertise. Indeed, without rigorous implementation of the process, the drops produced may have non-homogeneous sizes, which is prejudicial to the analysis.

SUMMARY OF THE INVENTION

The aim of the present invention is that of remedying these drawbacks of the previous methods.

In particular, in various embodiments, the present invention provides a process for treating and analysing a solution containing a biological material, using a microfluidic method wherein the solution is divided into a plurality of drops, which is quicker to implement than previous processes, more effective, simpler and less costly, requiring less training of the operators to implement the process, and suitable for usefully treating and analysing a greater proportion of the biological material used.

A further aim of the present invention is that of providing a microfluidic circuit suitable for implementing such a process.

The aim of the invention is in particular, according to at least one of the embodiments thereof, that of providing such a process, and the microfluidic circuit suitable for implementing same, suitable for conducting digital PCR using drops that is simpler, more effective and less costly that the processes according to the prior art.

DESCRIPTION OF THE INVENTION

These aims, along with others which will emerge more clearly hereinafter, are achieved using a microfluidic process for treating and analysing a solution containing a biological material, the process comprising, according to the invention, the following steps:
  i. introducing the solution into microchannels of a microfluidic circuit;
  ii. detaching drops of the solution in a carrier fluid, caused by the divergence of the microchannel walls, coupled with the effects of the surface tension of the solution;
  iii. moving at least a portion of the drops in the carrier fluid to at least one drop storage zone in the microfluidic circuit, caused by the divergence of the microchannel walls, coupled with the effects of the surface tension of the drops;
  iv. applying a treatment to the drops situated in the storage zone(s);
  v. analysing the drops situated in the storage zone(s).

This process advantageously enables the reaction induced by the treatment to take place independently in each of the drops. It can be implemented particularly easily, in a single microfluidic circuit wherein the various steps are carried out. Moreover, the drops may be produced regardless of the presence or absence of a carrier fluid flow or not. The size of the drops, in particular, is not closely dependent on a movement of the carrier fluid, and is homogeneous from the start of the formation thereof. It is thus possible for all or almost all the sample used to undergo treatment and analysis.

For this, the microchannels of the microfluidic circuit are configured so that the solution circulates therein between walls diverging from each other, causing a variation in the confinement of the solution. The divergence of each wall may be progressive (sloped walls) or abrupt (step). The surface tension of the solution, i.e. the interfacial tension between the solution and the carrier fluid with which it is in contact, forces the flow of solution to take a shape that accounts for this variable confinement, resulting in drop separation.

This method for separating drops, wherein the surface tension of the solution is used to cause the detachment of the drop, thus differs radically from the methods requiring a flow of carrier fluid to create a drop by shearing the solution, by opposing the surface tension of the solution which on the contrary tends to unite the solution. It also has the advantage of not requiring balancing of the flow of carrier fluid with the flow of solution, which simplifies the process.

The movement of the drops is also caused by the divergence of the walls coupled with the effects of the surface tension of the drops. It may be caused directly, a drop moving between walls diverging from each other, under the effect of the surface tension thereof, or indirectly, the drop being propelled by another drop, which in turn moves between the walls diverging from each other, under the effect of the surface tension thereof.

Finally, the drops are held, after the formation thereof and the movement thereof, in at least one storage zone, which is a zone wherein they may enter, but in which they cannot come out without external intervention (for example a flow of carrier fluid providing sufficient energy thereto to come out). They may thus be very readily subjected to treatment or analysis.

Advantageously, the carrier fluid wherein the drops are detached and moved is substantially static.

The production and movement of the drops are thus more reliable, in that they are defined merely by the design of the walls of the microchannels, without being disturbed by a flow of carrier fluid. Obviously, the carrier fluid, although substantially static, is subject to slight disturbances caused by the movement of the drops.

According to one advantageous embodiment of the invention, the treatment applied to the drops comprises variations of the temperature of the drops.

Preferentially, in this case, the temperature variations are applied to the entire microfluidic circuit containing the drops. They may also be applied to sub-regions or to individual drops, for example in succession.

These temperature variations can indeed be readily applied to the microfluidic circuit and to all the drops contained therein. Transfers of the drops from one vessel to another are thus avoided.

The temperature variations, or thermocycling, may for example be suitable for performing polymerase chain reaction amplification. Further treatments may also be applied, such as for example an incubation, consisting of holding the drops, for a sufficiently long time, at temperature conditions enabling a reaction to take place.

Preferentially, the analysis of the drops is an optical analysis.

This analysis may be carried out readily, via the walls of the microfluidic circuit, without any transfer of drops being required.

According to one advantageous embodiment of the invention, at least one of the storage zones consists of a zone wherein the drops have a lower surface energy than in the adjacent zones.

In this way, the design of the microchannels of the microfluidic circuit is suitable for holding the drops in the storage zone, which may also be referred to as the trapping zone, under the effect of the surface tension thereof. They are thus effectively held in this storage zone regardless of any flow of carrier fluid, as long as this flow of carrier fluid or another external action, for example the propulsion of another drop, provides sufficient energy to raise the surface energy of the drop to a level for which it may enter a zone surrounding the storage zone.

Advantageously, the biological material contained in the solution comprises at least one nucleic acid, and the treatment applied to the drops is a polymerase chain reaction amplification, suitable for increasing the concentration of at least one sequence of said nucleic acid.

The process according to the invention is thus suitable for performing digital polymerase chain reaction amplification using drops, which is simpler and more effective than those used in the prior art.

The invention also relates to a microfluidic circuit, wherein microchannels suitable for containing fluids are defined, the circuit comprising at least one device for forming drops of a solution in a carrier fluid, and at least one zone for storing the drops produced. According to the invention, the devices for forming drops comprise wall portions of the microchannels, diverging so as to detach a drop of the solution under the effect of the surface tension of the solution, and the microfluidic circuit comprises means for guiding the drops comprising wall portions of the microchannels, diverging so as to move the drops to the storage zone under the effect of the tension of the drops.

This circuit is particularly suitable for implementing the process described above, particularly readily. Indeed, no flow of carrier fluid is required in this circuit, since the sole introduction of the solution into the circuit automatically gives rise to the division thereof into drops and the movement of these drops to the storage zone where they can be treated and analysed.

Preferentially, at least one of the storage zones consists of a zone of a microchannel wherein the walls of said microchannel are further from each other than in the adjacent zones.

This storage zone may for example be defined in a chamber, wherein the drops are only confined by an upper wall and a lower wall. A zone in this chamber wherein these two walls are further from each other enables the drops to be less confined therein. This zone then retains the drops and forms a storage zone.

According to one advantageous embodiment, the microfluidic circuit contains at least two separate storage zones.

It is thus possible to treat and analyse a plurality of groups of separate drops simultaneously.

Advantageously, the microfluidic circuit comprises at least two devices for forming drops, each being suitable for forming drops of different volumes.

In this way, the circuit is suitable for treating and analysing drops of a plurality of sizes simultaneously.

Advantageously, in this case, the means for guiding the drops are designed so as to guide the drops of different volumes to separate storage zones.

According to one advantageous embodiment, at least one of said storage zones is designed so as to only receive one drop.

In this case, each drop may be held in an individual storage, or trapping, zone. This enables superior positioning of drops, particularly suitable for facilitating the analysis thereof. In this case, the drops not being, in contact with each other during the treatment and analysis thereof, they are not liable to merge. It is thus possible in this case, to reduce the surfactant properties of the carrier fluid to no disadvantage.

According to a further advantageous embodiment, at least one of the storage zones is designed so as to receive drops in one layer.

Such an embodiment is suitable for facilitating the analysis of the drops.

According to a further advantageous embodiment, at least one of the storage zones is designed so as to distribute the drops contained therein on at least two superimposed layers.

Such an embodiment, requiring an extra-high storage zone, is suitable for treating and analysing a greater number of drops.

Preferably, the microfluidic circuit consists, at least in part, of a transparent material suitable for viewing at least one of the storage zones, from outside the circuit.

The optical analysis of the drops after the treatment thereof is thus facilitated.

BRIEF DESCRIPTION OF THE DRAWINGS

The present invention will be understood more clearly on reading the following description of preferred embodiments, given for the purposes of illustration and not limitation, and accompanied by figures, wherein.

DETAILED DESCRIPTION OF ONE EMBODIMENT

Microfluidic Circuit

Figure 1:
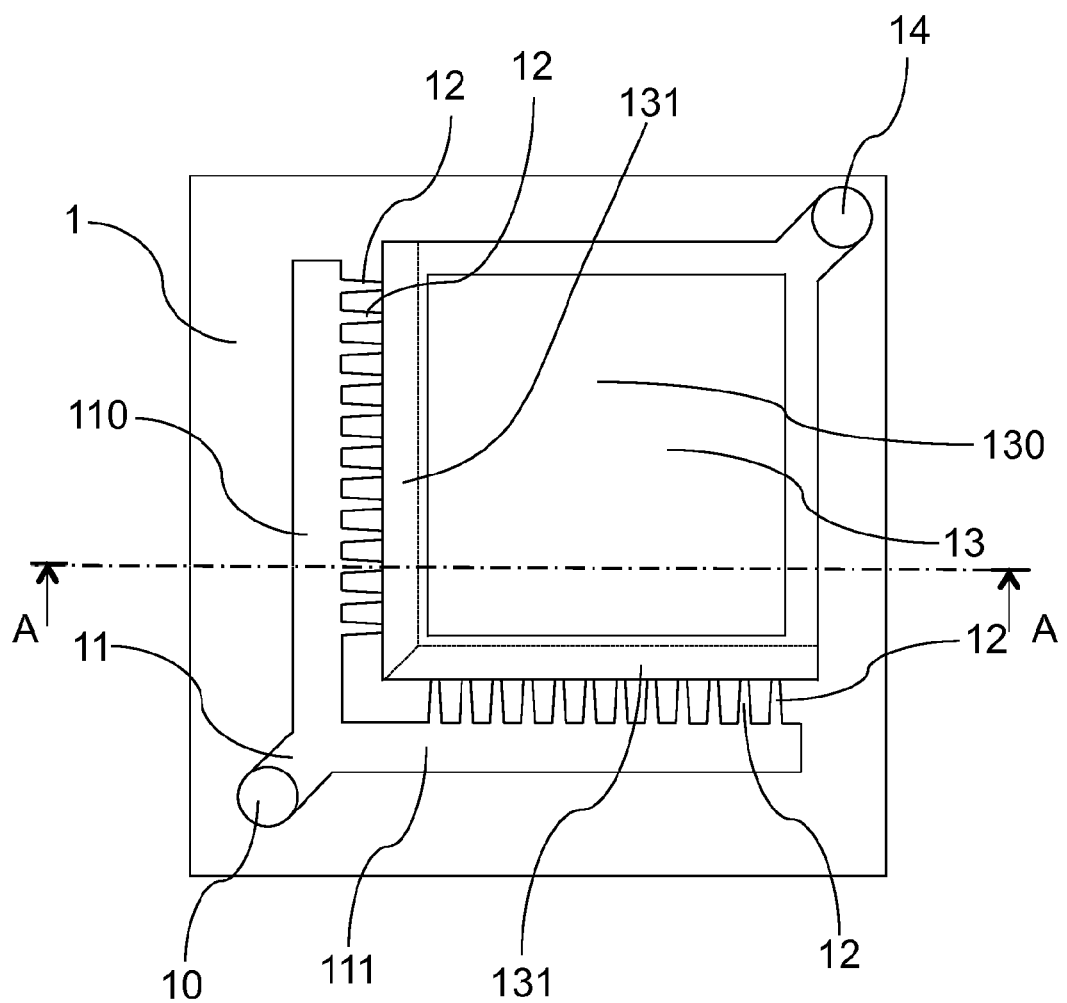
FIG. 1 is a top view horizontal projection of a microfluidic circuit suitable for implementing a process according to a first embodiment of the invention.
Figure 2:
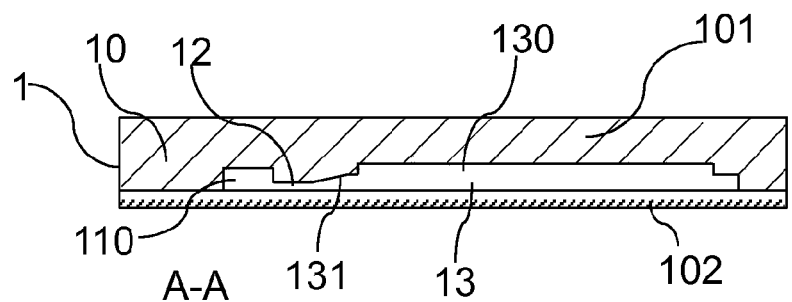
FIG. 2 is a cross-section of the microfluidic circuit in FIG. 1.

FIG. 1 is a top view horizontal projection of a microfluidic circuit 1 suitable for implementing a process according to a preferential embodiment of the invention. This horizontal projection shows the various microfluidic channels provided inside this microfluidic circuit. A cross-section of this microfluidic circuit 1 is also represented in FIG. 2.

This microfluidic circuit 1 may consist of two overlaid plates, glued to each other. In this way, the circuit 1 consists of a plate 102, which may for example be a transparent microscope slide, and a plate 101, wherein the face in contact with the plate 102 is etched so as to define microchannels between the two plates which are overlaid and glued to each other. The plate 101 may consist of a polymer material. Preferably, the material forming at least one of the two plates is transparent, so as to facilitate the observation of the fluids in the microchannels. In this case, the observation of the circuit 1 is suitable for viewing the microchannels by means of transparency, as represented in FIG. 1.

The dimensions of these microchannels may be chosen freely by adapting the width and depth of the etching in the etched plate. For example, the microchannels may have a width of approximately 100 μm and a depth of approximately 50 μm. These microchannels may also have larger, or on the other hand smaller, dimensions, so as to adapt to the characteristics of various fluids, or the sizes of the drops to be handled. It should be noted that microfluidic circuits manufactured based on other methods known to those skilled in the art may obviously be used to implement the invention.

These microchannels are normally dimensioned so that the walls thereof apply a load confining the solution or on the drops circulating therein. In most microchannels, the drops are thus confined by the upper, lower, right and left walls. Some microchannels, hereinafter referred to as "chambers", are however dimensions so as only to apply a load in one dimension, two of the substantially parallel walls thereof (generally the upper wall and the lower wall) being close together to confine the drops, and the other walls being sufficiently distant so as not to confine the drops.

The microfluidic circuit 1 should, prior to the use thereof, be filled with an inert fluid, hereinafter referred to as carrier fluid, which is not miscible with the fluids to be handled in the circuit. This carrier fluid is generally oil, suitable for being supplemented with a surfactant additive product suitable for preventing the spontaneous merging of drops of solution handled, if they come into contact. This surfactant additive may sometimes be unnecessary, according to the characteristics of the oil used as a carrier fluid and the solution to be treated and analysed.

The microfluidic circuit 1 comprises a supply microchannel 11, divided into two supply branches 110 and 111, extending perpendicularly to each other. This microchannel 11 is connected to a supply hole 10 which is perforated in one of the plates forming the microfluidic circuit 1, and wherein the needle of a syringe or the end of a pipette may be inserted so as to inject a fluid into the supply channel 11.

The chamber 13 also has a discharge opening connected to a hole 14 perforated through one of the plates of the circuit 1. This opening is particularly suitable for discharging a portion of the carrier fluid, when the total volume of fluid inserted into the microchannels is greater than the volume of these microchannels.

Drop Formation

The two supply branches 110 and 111 are each connected to a plurality of drop-forming nozzles 12. For the purpose of clarity, the nozzles have been represented in FIG. 1 with greater dimensions than the normal dimensions thereof. Moreover, only some of the nozzles 12 are referenced in FIG. 1.

These drop-forming nozzles 12 are microchannels, or conduits having a small cross-section suitable for being supplied with fluid via the first end thereof and allowing the passage of a small flow of this fluid towards a second end. FIG. 3A, FIG. 4A, FIG. 5A and FIG. 6A represent in detail the horizontal projection of a drop-forming nozzle 12 and the chamber wherein it opens, at several stages of the formation of a drop of fluid. This nozzle and this chamber are also represented in detail from the cross-sections in FIGS. 3B, 4B, 5B and 6B, corresponding respectively to the views in FIG. 3A, FIG. 4A, FIG. 5A and FIG. 6A. For the purpose of clarity, the carrier fluid filling the channels of the circuit 1 is not represented in these figures.

As shown in these figures, the second end of the nozzle 12 opens onto a central chamber 13, having an upper surface etched in the plate 101 and a lower surface consisting of the plate 102. In the vicinity of the second end of the nozzle 12, the upper surface of the chamber 13 has an inclined zone 131, such that the two surfaces of the chamber 13 diverge when they move away from the second end of the nozzle 12. This divergence of the walls enables the confinement applied to the solution to decrease along the trajectory thereof, after the passage thereof in the nozzle 12.

It should be noted that, according to one possible alternative embodiment not represented in the figures, the inclined zone may be replaced by a zone forming a succession of a plurality of steps in the chamber surface, without leaving the scope of the invention. Indeed, those skilled in the art know that such a succession of steps has the same technical effect as an inclined zone. Similarly, it would possible according to further embodiments, for the walls to diverge in width rather than diverge in height.

Figure 3A:
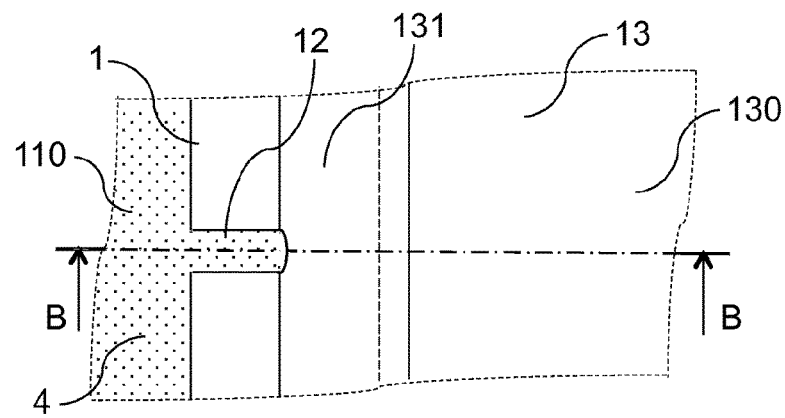
FIG. 3A is a detail of the horizontal projection in FIG. 1, at different stages of use of the microfluidic circuit.
Figure 3B:
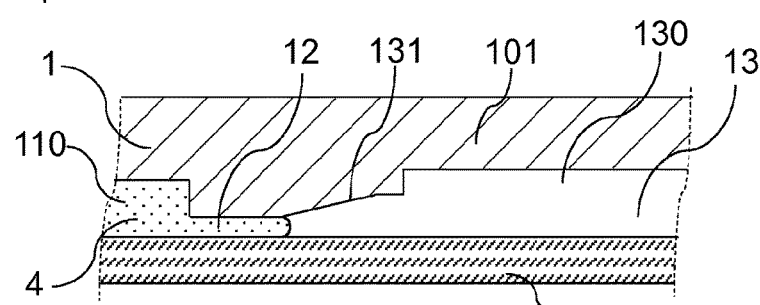
FIG. 3B is a cross-section corresponding to FIG. 3A.
Figure 4A:
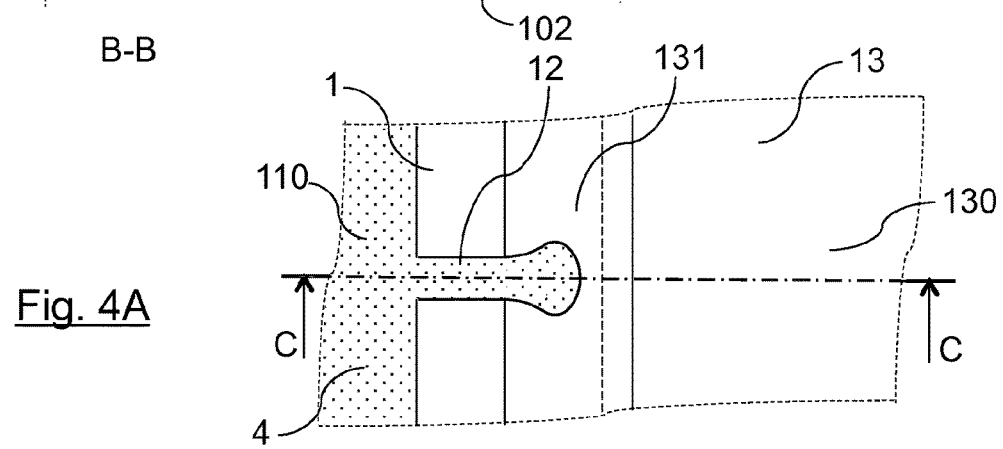
FIG. 4A is a detail of the horizontal projection in FIG. 1, at different stages of use of the microfluidic circuit.
Figure 4B:
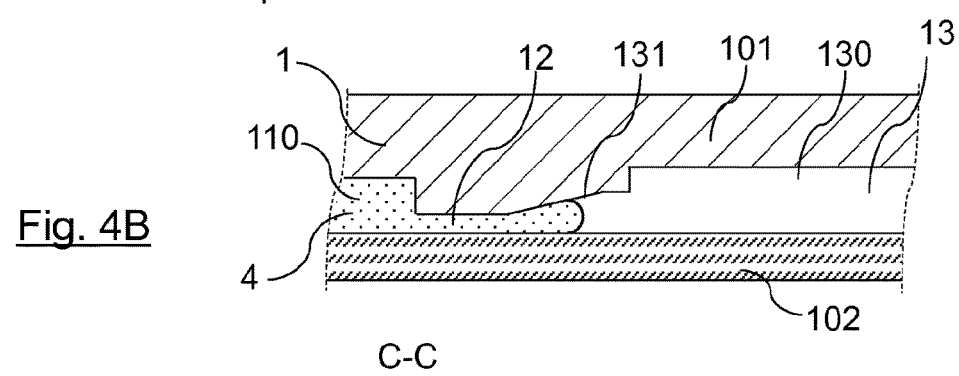
FIG. 4B is a cross-section corresponding to FIG. 4A.

As shown in FIG. 3A and FIG. 3B, when a fluid 4, for example a solution containing a biological material, is introduced into the microfluidic circuit 1 via the hole 10, it fills the supply branch 110 and the nozzle 12. As the introduction of the fluid 4 into the hole 10 continues, the leading edge of the flow of fluid 4 advances into the chamber 13, as shown in FIG. 4A and FIG. 4B. This fluid is then confined between a lower surface, consisting of the plate 102, and an upper surface, consisting of the inclined zone 131, diverging from each other as they move away from the nozzle 12.

Figure 5A:
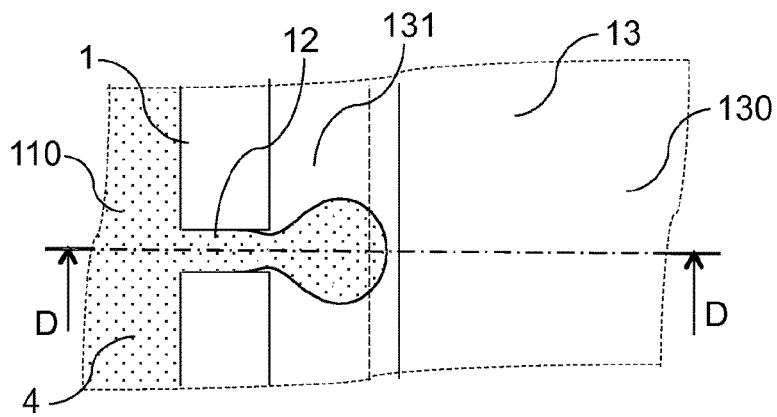
FIG. 5A is a detail of the horizontal projection in FIG. 1, at different stages of use of the microfluidic circuit.
Figure 5B:
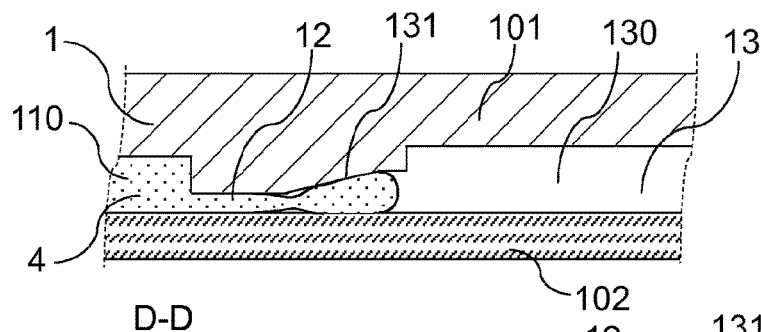
FIG. 5B is a cross-section corresponding to FIG. 5A.
Figure 6A:
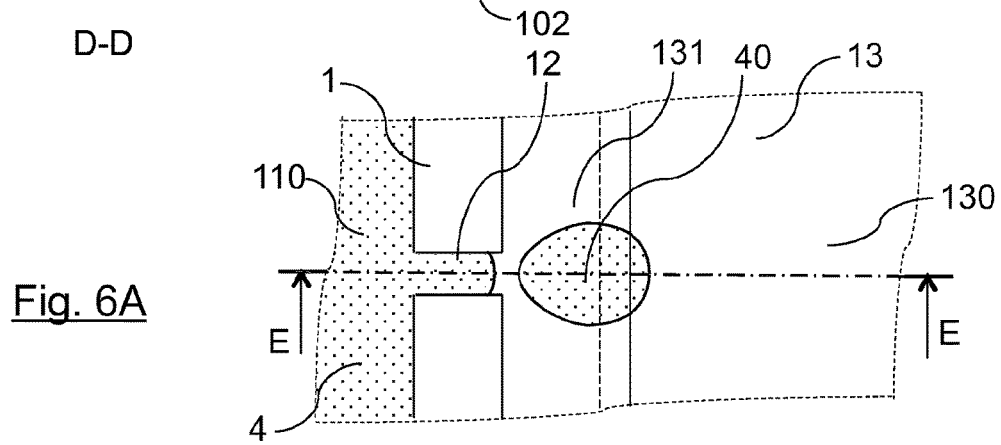
FIG. 6A is a detail of the horizontal projection in FIG. 1, at different stages of use of the microfluidic circuit.
Figure 6B:
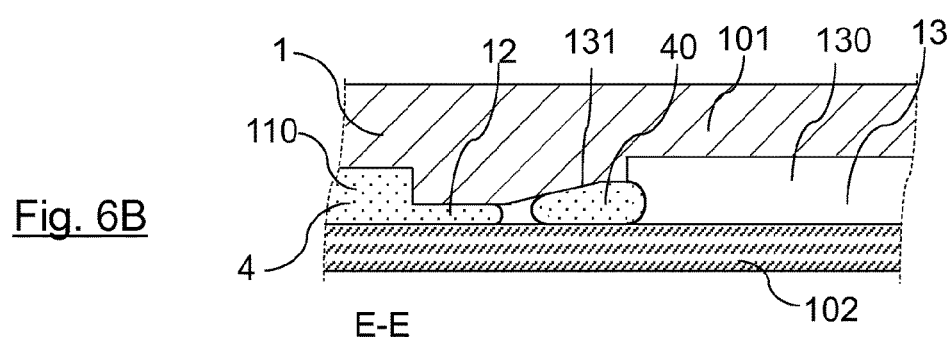
FIG. 6B is a cross-section corresponding to FIG. 6A.

This divergence of the surfaces tends to attract the fluid 4 far away from the nozzle 12. Indeed, the fluid tends to adopt a shape as close as possible to a sphere, which is the shape wherein the surface energy thereof is minimal. It thus tends to move towards spaces wherein it is less confined. This attraction deforms the leading edge of fluid, as shown in FIG. 5A and FIG. 5B, and induces by means of this deformation the detachment of a drop 40, as represented in FIG. 6A and FIG. 6B, from a critical size determined by the geometric parameters.

In this way, the shape of the microchannels of the microfluidic circuit 1, and more specifically the succession of a drop-forming nozzle 12 and a chamber 13 wherein the surfaces diverge from each other when moving away from the nozzle 12, is suitable for forming drops 40 of fluid 4, without any flow of carrier fluid being required. Indeed, the only action required to form these drops is the introduction of the fluid 4 into the hole 10 with a sufficient pressure.

Alternatively, the drops may also be formed by applying a suction (or a negative pressure) at the outlet 14 of the microfluidic circuit, after introducing the fluid 4 into the hole 10. The drops are then formed in the same way.

It should be noted in this respect that the feed pressure of the fluid 4 in the microfluidic circuit 1 has only a very slight influence on the size of the drops 40 formed. It was thus demonstrated by the inventors that multiplying the feed pressure of the fluid 4 by one thousand merely multiplies the size of the drop produced by two. The microfluidic circuit 1 thus makes it possible to produce drops 40 wherein the size primarily results from the geometric characteristics of the microchannels (and particularly of the cross-section of the nozzle 12 and the slope of the inclined zone 131) and the viscosity of the fluid 4. Each nozzle 12 may thus, when supplied upstream with a continuous flow of fluid, herein by the fluid from the supply branches 110 and 111, supply drops of homogeneous size of the same fluid downstream.

Such drop-forming nozzles 12, which are suitable for forming a train of drops from a continuous flow of fluid without needing to have a flow of carrier fluid, are described in the document WO 2011/121220, held by the applicants.

Twenty-four nozzles 12 are represented on the microfluidic circuit 1 in FIG. 1. It is however obvious that more numerous similar nozzles, and of smaller size, may be used in other microfluidic circuits suitable for implementing the invention. By way of example, a microfluidic circuit comprising 256 nozzles each 50 μm in height and 100 μm in width, is suitable for splitting a sample of approximately 20 μl of solution into approximately 100,000 drops in two minutes.

It should be noted that, according to further possible embodiments, the nozzles may be distributed around three sides, or the four sides of a rectangular chamber, or be distributed around a portion of or the entire periphery of a chamber having a different shape, for example round, hexagonal, etc. These very numerous alternative embodiments are enabled by the method for producing drops without a flow of carrier fluid, enabling simultaneous production of a very large number of drops without needing to envisage the circulation and discharge of a large volume of carrier fluid.

Drop Storage

Since each of the drop-forming nozzles 12 opens into the same chamber 13, all of the drops produced are concentrated in a storage zone of this chamber. The term "storage zone", or "trapping zone", denotes in the present description a zone of the microfluidic circuit wherein a drop can enter, but wherein it cannot come out without external intervention.

In the embodiment represented, a zone is etched as a hollow in the upper surface of this chamber 13, so as to form a drop storage zone 130, situated in the centre of the chamber 13. Around the storage zone 130, the chamber 13 has upper and lower surfaces which are preferably parallel and which are sufficiently close so that the drops positioned in the chamber are confined between these two surfaces, without being able to adopt the spherical shape corresponding to a minimal surface energy.

Due to the hollow etching, the distance between the upper surface of the chamber and the lower surface is greater (for example approximately 50 μm) in the storage zone than in the adjacent zones. A drop positioned in this storage zone can thus adopt a more compact shape than a drop confined between the upper and lower surfaces of the chamber 13, around the storage zone 130. Consequently, a drop found in the storage zone has a lower surface energy than a drop found outside this zone. A drop positioned in this storage zone thus cannot come out of said zone without being supplied with energy to increase the surface energy thereof.

It should be noted that the technique for trapping drops in the microfluidic circuit is described in the document WO 2011/039475, held by the applicants.

The storage zone 130 thus forms a space wherein the drops are held, and is preferably dimensioned such that the drops are arranged therein in one layer, in two dimensions. All the drops thereof contained in this zone are thus directly visible from outside the microfluidic circuit, due to the transparency of at least one of the surfaces of the chamber.

It is however possible, according to further embodiments, to use a storage zone wherein the upper surface and the lower surface are at a sufficient distance to receive drops distributed into a plurality of layers.

Preferably, the storage zone 130 is situated in the vicinity of the location where the drops are formed. In this way, the drops are introduced into this storage zone 130 from the formation thereof, without any external means being required to move the drops to this zone. Indeed, the configuration of the walls of the chamber 13, and particularly the divergence of the walls at the inclined zone 131 and the edges of the storage zone 130, enables each drop to move under the effect of the surface tension thereof to this storage zone. It is also possible for the drops to move to the chamber 13, to the storage zone, propelled by other drops.

Treatment and Analysis of a Solution in this Microfluidic Circuit

The microfluidic circuit 1 is, prior to the use thereof, filled with a carrier fluid. To carry out a treatment and an analysis of a solution containing a biological material, an operator introduces this solution via the supply hole 10. This introduction is performed merely by adjusting the end of a pipette or the needle of a syringe in the hole 10 before discharging this fluid by pressing on the syringe or pipette. The fluid then flows into the supply channel 11, and then into the branches 110 and 111 thereof. It then passes through the various nozzles 12, at the outlet whereof it is split into drops flowing into the chamber 13. Due to the large number of nozzles 12 distributed along the branches 110 and 111 of the supply channel, a large number of drops may be created simultaneously. These drops are trapped and retained in the storage zone 130, and quickly fill the entire storage zone.

It should be noted that the drops are produced in a particularly simple and effective manner. Indeed, the operator only needs to introduce the solution into an orifice, without needing to balance the flow rate of this fluid with the flow rate of a carrier fluid. Moreover, the pressure applied by the operator onto the syringe or pipette has only a very slight influence on the size of the drops produced. The operator can thus inject the solution into the hole 10 without taking special precautions to ensure perfectly constant pressure. The drops formed by the nozzles 12, from the start of drop formation, in any case have homogeneous dimensions.

The operator can monitor the filling of the chamber 13 and stop injecting the solution when the storage zone 130 is completely filled, to prevent the drops of the solution from escaping via the discharge opening connected to the hole 14.

If the volume of sample suitable for creating sufficient drops to fill the storage zone is known, it is also possible to inject precisely this volume of the solution, to avoid losing a portion of the sample. In this case, it may be useful to inject a small quantity of carrier fluid into the hole 10 after injecting solution, so as to push back the solution remaining in the supply channel 11 and the branches 110 and 111 thereof to the chamber 13.

When the storage zone 130 of the chamber 13 is filled with drops of the solution to be treated and analysed, the operator can remove the pipette or syringe from the hole 10. Due to the retention of the drops in the storage zone 130, the microfluidic circuit 1 may then be handled by the operator without any risk of the drops escaping. The entire microfluidic circuit 1 may for example be placed in a heating device suitable for the thermocycling thereof, or any other heat treatment, without any risk of losing a portion of the sample of solution divided into drops. It is also possible to carry out other types of treatment, in addition to or instead of a heat treatment.

After a treatment, an optical analysis of the drops may be carried out very readily, all the drops contained in the storage zone 130 of the chamber 13 being advantageously visible via a transparent face of the microfluidic circuit 1. This analysis may, advantageously, be performed in an automated manner.

Embodiments with a Plurality of Storage Zones

A large number of alternative embodiments of this process may be implemented without leaving the scope of the invention, particularly using microfluidic circuits specially designed to adapt to varied experimental conditions.

Figure 7:
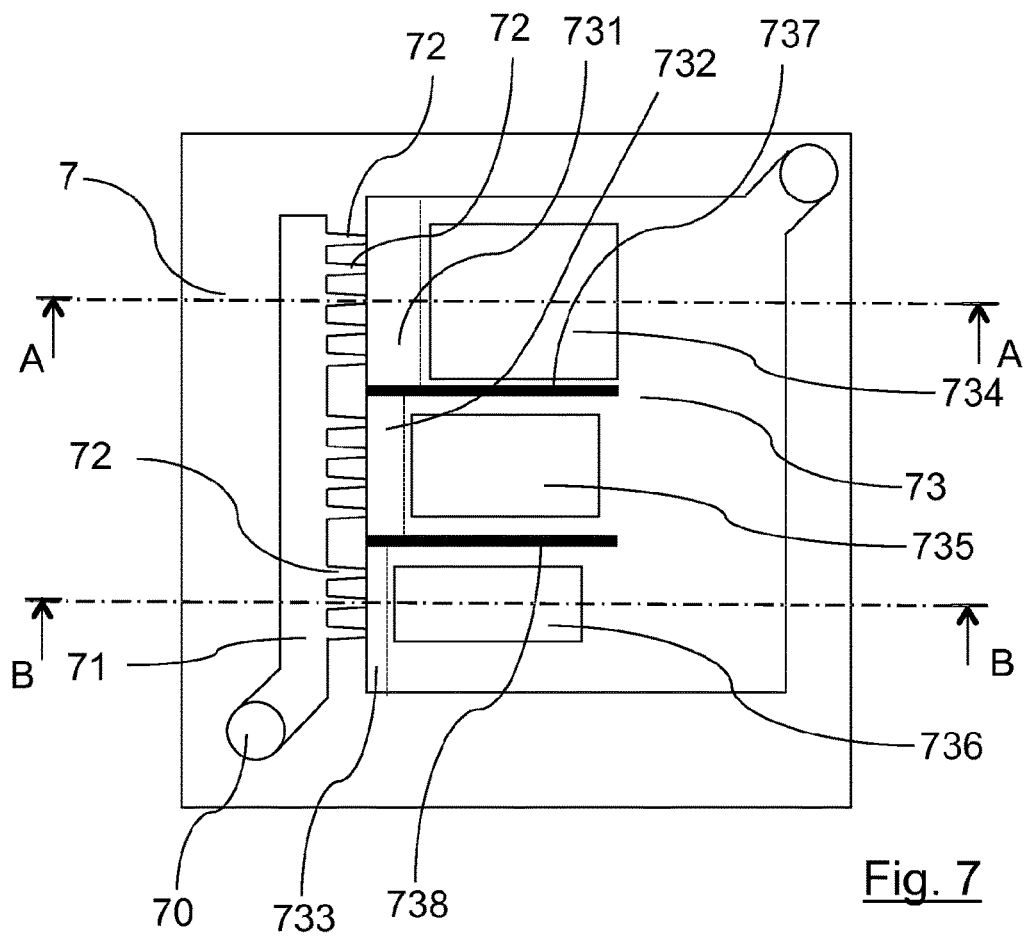
FIG. 7 is a horizontal projection of a microfluidic circuit suitable for implementing a process according to a second possible embodiment of the invention.
Figure 8:
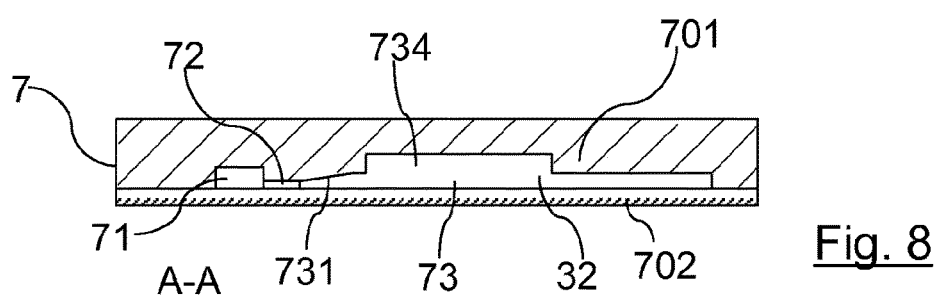
FIG. 8 is a cross-section of a microfluidic circuit suitable for implementing a process according to a second possible embodiment of the invention.
Figure 9:
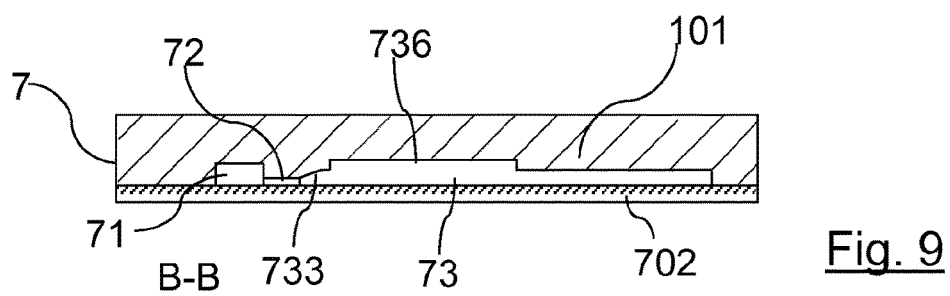
FIG. 9 is a cross-section of a microfluidic circuit suitable for implementing a process according to a second possible embodiment of the invention.

In this way, FIG. 7 is a top view horizontal projection of a microfluidic circuit 7 suitable for implementing a process according to a second possible embodiment of the invention. Cross-sections of this microfluidic circuit 7 are also represented in FIG. 8 and FIG. 9. Like the microfluidic circuit 1, the microfluidic circuit 7 consists of a transparent plate 702 and an etched plate 701 so as to define microchannels between the two plates, when they are overlaid and glued to each other.

This microfluidic circuit 7 comprises a supply hole 70 connected to a supply microchannel 71. Twelve drop-forming nozzles 72 are connected to this supply microchannel 71, and open onto a chamber 73. In the embodiment represented, all the nozzles 72 (which, for the purpose of clarity, are not all referenced in FIG. 7) are identical. They are preferably of the same type as the nozzles 12 of the microfluidic circuit 1.

In this embodiment, the upper surface of the chamber 73 has a plurality of inclined zones, respectively 731, 732 and 733, having different slopes. Each of these inclined zones is situated in the vicinity of the end of some of the nozzles 72. In this way, the inclined zone 731, particularly visible in the cross-section in FIG. 8, has a relatively low slope, such that the upper and lower surfaces of the chamber 73 diverging slightly from each other when they move away from the nozzles 72. On the other hand, the inclined zone 733, particularly seen in the cross-section in FIG. 9, has a relatively high slope, such that the lower and upper surfaces of the chamber 73 diverge considerably on moving away from the nozzles 72. The inclined zone 732 has an intermediate slope.

Due to the different slopes, the drops produced by the nozzles 72 and the surfaces of the chamber 73 are of different sizes for each of the inclined zones. In this way, the drops produced at the inclined zone 731 are larger than those produced at the inclined zone 732, in turn larger than those produced at the inclined zone 733.

Three drop storage zones are defined by etching in the upper surfaces of the chamber 73. The storage zone 734 is situated in the vicinity of the inclined zone 731 so as to collect the drops formed at this inclined zone. Similarly, the storage zones 735 and 736 are positioned, respectively, in the vicinity of the inclined zones 732 and 733. Advantageously, the dimensions of each of these storage zones is adapted to the dimensions and the quantity of the drops that they are intended to receive.

In the embodiment represented, dividing walls 737 and 738, raised along the entire height of the chamber 73, are suitable for partially partitioning the chamber to prevent some of the drops from moving to a storage zone for which they are not intended.

In this way, the microfluidic circuit 7 is suitable for preparing, simultaneously, samples of drops of different sizes of the same solution. These samples may then undergo the same treatments, before being analysed. Such a process may be useful, for example, for analysing a solution for which the size of drops suitable for obtaining an optimal result is not known.

Obviously, those skilled in the art may readily implement alternatives of this embodiment, for example using drop-forming nozzles of different sizes opening onto the same inclined zone, without leaving the scope of the present invention.

Microfluidic Circuit with a Plurality of Identical Storage Zones

Figure 10:
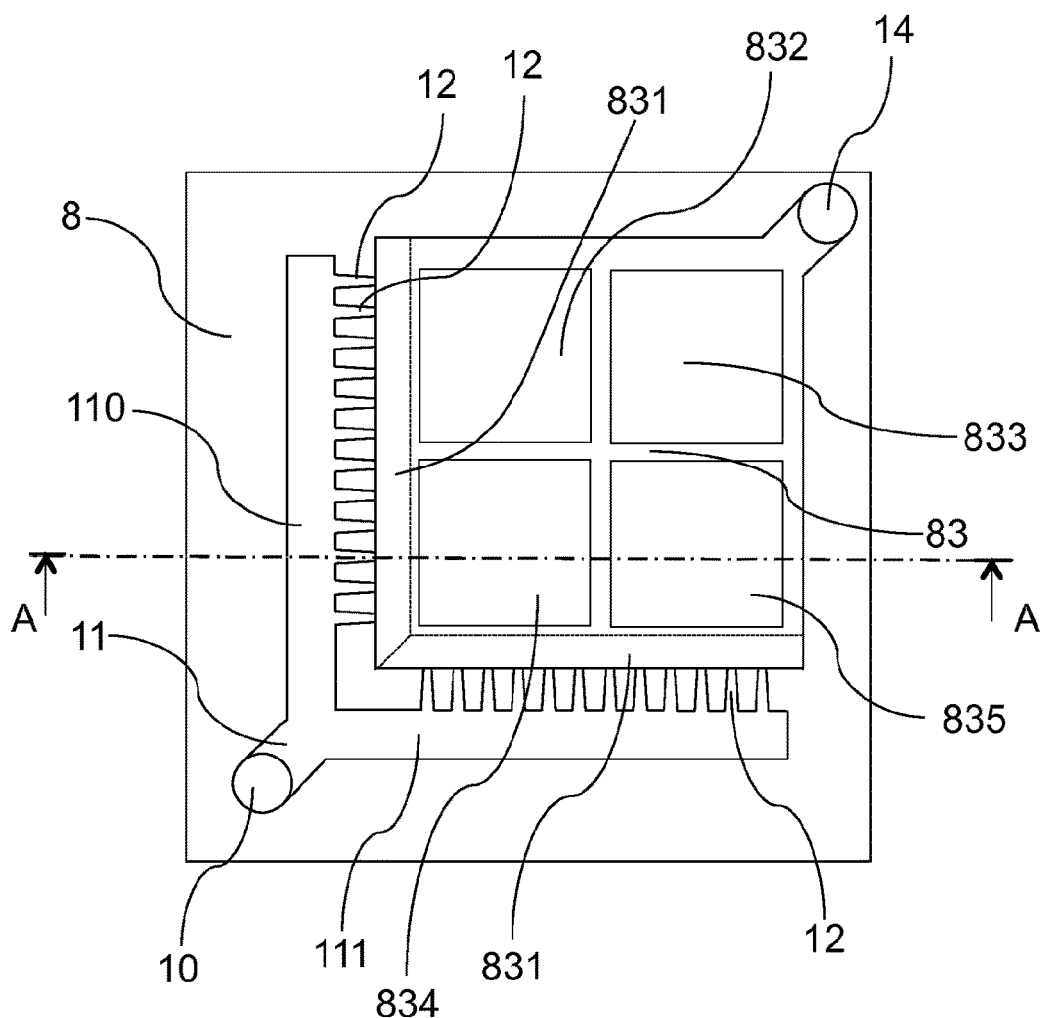
FIG. 10 is a horizontal projection of a microfluidic circuit suitable for implementing a process according to a third possible embodiment of the invention.
Figure 11:
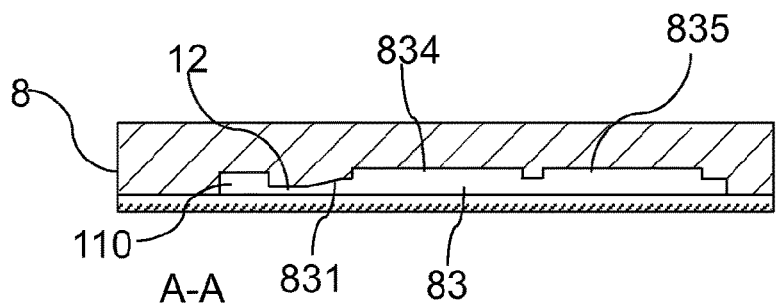
FIG. 11 is a cross-section of a microfluidic circuit suitable for implementing a process according to a third possible embodiment of the invention.

FIG. 10 is a top view horizontal projection of a microfluidic circuit 8 suitable for implementing a process according to a third possible embodiment of the invention. A cross-section of this microfluidic circuit 8 is also represented in FIG. 11. This circuit 8 is mostly identical to the microfluidic circuit 1. It particularly comprises the same supply hole 10, the same supply microchannel 11 being divided into two supply branches 110 and 111, and the same drop-forming nozzles 12. The central chamber 83, wherein the drop-forming nozzles 12 open, has identical inclined zones 831 to the inclined zones 131 of the microfluidic circuit 1.

In this embodiment, the upper wall of the chamber 83 is etched so as to define, not one, but four separate drop storage zones. These four storage zones 832, 833, 834 and 835 are, in the embodiment represented, identical. They have however, for experimental purposes, different dimensions, for example to contain drops distributed into a different number of layers.

During drop production, the drops fill the different storage zones, if need be propelled towards these storage zones by other drops.

Microfluidic Circuit with Individual Drop Trapping

Figure 12:
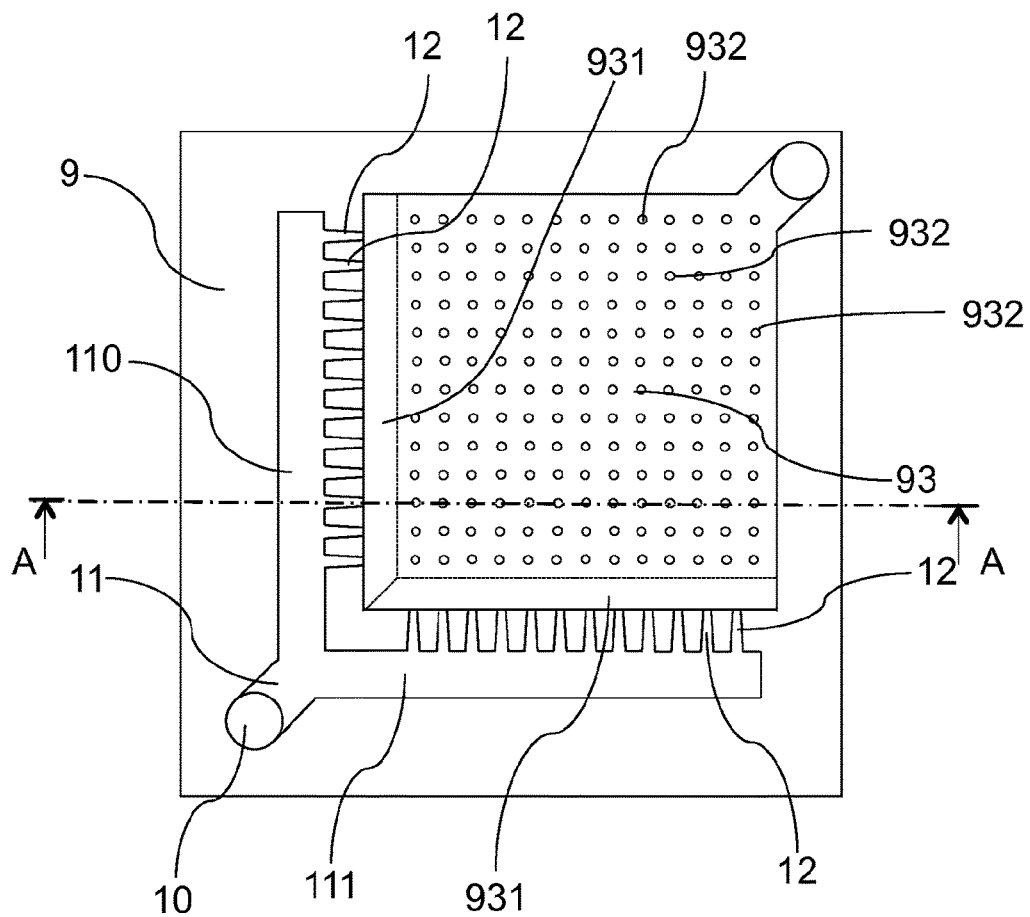
FIG. 12 is a horizontal projection of a microfluidic circuit suitable for implementing a process according to a fourth possible embodiment of the invention.
Figure 13:
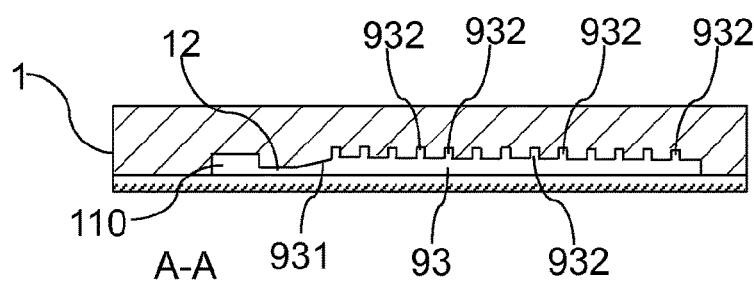
FIG. 13 is cross-section of a microfluidic circuit suitable for implementing a process according to a fourth possible embodiment of the invention.

FIG. 12 is a top view horizontal projection of a microfluidic circuit 9 suitable for implementing a process according to a fourth possible embodiment of the invention. A cross-section of this microfluidic circuit 9 is also represented in FIG. 13. This circuit 9 is also mostly identical to the microfluidic circuit 1. It particularly comprises the same supply hole 10, the same supply microchannel 11 being divided into two supply branches 110 and 111, and the same drop-forming nozzles 12. The central chamber 93, wherein the drop-forming nozzles 12 open, has identical inclined zones 931 to the inclined zones 131 of the microfluidic circuit 1.

The upper wall of the chamber 93 is etched so as to define a plurality of small holes 932. These holes 932 (which are not all referenced in FIG. 12 and FIG. 13, for the purpose of clarity) may have a small diameter, for example between approximately 10% and 120% of the diameter of a drop. Each of these holes 932 forms a storage zone, or a "trap", capable of receiving a single drop.

When the drops formed fill the chamber 93, they are placed on each of these storage zones 932, if need be propelled from one storage zone to another by another drop. It is also possible, according to one alternative of this embodiment, that the upper wall of the chamber 93 is not perfectly parallel with the lower wall thereof, so as to form a slight slope favouring the movement of the drops to the storage zones 932 which are furthest from the drop-forming nozzles 12.

Each of the storage zones 932 is thus rapidly occupied by a single drop. The microfluidic circuit 9 is thus suitable for producing, treating and analysing a plurality of drops each occupying a very specific position, known in advance. Such a drop arrangement may considerably facilitate the optical analysis of the results of a treatment performed on the drops.

Moreover, in this embodiment, the drops produced do not remain in prolonged contact with each other. Indeed, the positions of the different storage zones 932 are advantageously chosen so that the trapped drops do not touch each other. This lack of prolonged contact between the drops reduces the risk of a plurality of drops merging into a single drop considerably. Consequently, in this embodiment, the use of a surfactant additive (surfactants used to prevent the coalescence of drops together), added to the carrier fluid, may prove to be unnecessary. In other cases, a low-performance surfactant additive may suffice. This embodiment is thus particularly advantageous in that it makes it possible to avoid the use of the highest-performance surfactant additives, which may be costly.

Advantages of the Invention Relative to Prior Solutions

The process according to the invention is thus suitable for rendering the treatment and analysis of a solution containing a biological material divided into drops quicker, more efficient, simpler and less costly.

Indeed, it is suitable for maximising the simplification of the preparation of the sample to be treated. It is simply necessary for the operator to inject the solution to be analysed into a suitable microfluidic circuit, without being concerned with the injection pressure, for this solution to be divided into drops confined in the circuit, ready to undergo a heat treatment and be analysed. Moreover, handling the circuit containing the drops does not require any special precautions.

This solution is thus simpler, quicker and less costly to use than the solutions according to the prior art requiring balancing of two fluid flows for producing drops of solution.

Furthermore, the process according to the invention enables practically all the solution used to be divided into drops suitable for being treated and analysed, which is advantageous relative to the solutions according to the prior art which give rise to the loss of a significant proportion of the treated solution.

Finally, the process according to the invention is suitable for producing drops without using a carrier fluid flow, the drop-forming nozzles may be distributed along a plurality of sides of the chamber intended to collect the drops. It is thus possible to distribute the drop-forming nozzles on two sides of a square chamber, as represented for example in the embodiment in FIG. 1. It is also possible to distribute these on three or four sides of such a chamber. It is also possible to distribute these around a chamber of a different shape, for example around almost the entire diameter of a circular chamber.

This possible distribution of a large number of drop-forming nozzles around a chamber, which is not possible with the solutions according to the prior art wherein drop production is accompanied by a carrier fluid flow, which should be allowed to be discharged, enables high efficiency in drop production. The process according to the invention is particularly suitable for carrying out, in a quicker, more efficient, simpler and less costly manner than with the processes according to the prior art, digital PCR using drops.

This process is also suitable for performing other types of treatment and analysis of solutions containing a biological material. In this way, it is for example possible to introduce into the microfluidic circuit a solution containing a small quantity of enzymes and a substrate capable of reacting with the enzyme. A certain time after drop formation, it is possible to analyse the drops optically (either automatically, or by means of a visual observation and a count) to determine the proportion of the drops wherein an enzyme reaction has taken place, and thus quantify the presence of enzyme. In this example, the treatment applied to the drops is an incubation, merely consisting of holding the drops for a sufficiently long time at temperature conditions enabling the enzyme reaction.

It is also possible, for example, to introduce into the microfluidic circuit a solution containing cells and markers capable of interacting with some of these cells. A certain time after drop formation, it is possible to analyse the drops optically (either automatically, or by means of a visual observation and a count) to determine the proportion of the drops wherein the cells have interacted with the markers, and thus quantify the presence of the cells to be characterised. Here again, the treatment applied to the drops is a mere incubation.

Finally, the microfluidic circuit according to the invention, suitable for implementing the process according to the invention, is particularly simple and inexpensive to manufacture per se. Numerous alternative embodiments of this circuit may be readily used. It is thus possible, for example, that the central chamber per se of the circuit forms the drop storage zone, provided that suitable means prevent the drops from coming out without external intervention.

The invention claimed is:

1. A microfluidic circuit, wherein microchannels suitable for containing fluids are defined, said circuit comprising at least one device for forming a plurality of drops of a solution in a carrier fluid, and at least one storage zone for storing drops produced by said microfluidic circuit;
   wherein said at least one device for forming drops further comprises said microchannels, wherein each of said microchannels comprise microchannel walls, said microchannel walls comprising diverging wall portions diverge, to detach drops of said solution under the effect of the surface tension of said solution to form said plurality of drops;
   wherein said storage zone comprises an upper surface, a lower surface and storage zone walls, wherein each said storage zone wall comprises a rectangular shaped step;
   wherein said at least one device for forming drops opens onto said step of said at least one storage zone,
   wherein said diverging wall portions of said microchannel walls causes at least a portion of said plurality of drops to move to said at least one storage zone;
   wherein the dimensions of said at least one storage zone are adapted to the dimensions and the quantity of the drops contained in said portion to concentrate said portion of drops;
   wherein said upper surface and lower surface are spaced further from each other than said microchannel walls.

2. The microfluidic circuit according to claim 1, wherein said microfluidic circuit further comprises at least two separate storage zones.

3. The microfluidic circuit according to claim 1, wherein said microfluidic circuit further comprises at least two devices for forming drops comprising drop-forming nozzles with different sections; each being suitable for forming drops of different volumes.

4. The microfluidic circuit according to claim 1, wherein said diverging wall portions for guiding the drops further comprises different inclined zones guiding said drops, wherein said drops are of different volumes, to separate storage zones.

5. The microfluidic circuit according to claim 1, wherein at least one of said storage zones is a hole of a diameter between 10% and 120% of the diameter of a member of said drops, said hole being adapted to receive only one drop.

6. The microfluidic circuit according to claim 1, wherein at least one of the storage zones further comprises predetermined dimensions adapted to receive said drops in a same layer.

7. The microfluidic circuit according to claim 1, wherein at least one of the storage zones further comprises a predetermined distance between its upper surface and its lower surface, said predetermined distance of said at least one storage zone sufficient to allow the drops contained in said at least one storage zone on at least two superimposed layers.

8. The microfluidic circuit according to claim 1, further comprising, at least in part, a transparent material suitable for viewing at least one of the storage zones, from outside the circuit.

* * * * *